United States Patent [19]

Latimer

[11] Patent Number: 5,243,862
[45] Date of Patent: Sep. 14, 1993

[54] CONFIRMATION OF HYDROGEN DAMAGE IN BOILER TUBES BY REFRACTED SHEAR WAVES

[75] Inventor: Paul J. Latimer, Lynchburg, Va.

[73] Assignee: The Babcock & Wilcox Company, New Orleans, La.

[21] Appl. No.: 710,271

[22] Filed: Jun. 4, 1991

[51] Int. Cl.$^5$ .................... G01N 29/08; G01N 29/20
[52] U.S. Cl. ............................ 73/600; 73/622; 73/634
[58] Field of Search .............. 73/600, 599, 592, 637, 73/638, 596, 622, 634

[56] References Cited

U.S. PATENT DOCUMENTS

| | | | |
|---|---|---|---|
| 4,127,035 | 0/1978 | Vasile | 73/629 |
| 4,289,030 | 9/1981 | Alers et al. | 73/637 |
| 4,307,612 | 0/1981 | Eisley et al. | 73/613 |
| 4,320,661 | 0/1982 | Peterson et al. | 73/643 |
| 4,593,568 | 0/1986 | Telford et al. | 73/623 |
| 4,685,334 | 8/1987 | Latimer | 73/622 |
| 4,890,496 | 1/1990 | Birring et al. | 73/599 |

OTHER PUBLICATIONS

Latimer, P. J., D. M. Stevens, and T. P. Sherlock, "ANDE Method for Hydrogen Damage Detection in Boiler Tubes," Proceedings of the EPRI Conference on Life Extension and Assessment of Fossil Plants, Washington, D.C., Jun. 2-4, 1986, EPRI C5-5208, pp. 1061-1076.

Latimer, P. J. and H. L. Whaley, "Electromagnetic Transducers for Generation and Detection of Ultrasonic Waves," *Acousto-Ultrasonics*, Edited by John C. Duke Jr., Plenum Publishing Corporation, 1988, (Presented at the Symposium on Acousto-Ultronics), Jul. 12-15, 1987, Virginia Polytechnic and State University, Blacksburg, Va.

Birring, A. S., D. G. Alcazar, J. J. Hanley and S. M. Gehl, "Ultrasonic Assessment of Creep and Hydrogen Damage in Fossil Plant Components", *Proceedings of the Second EPRI Fossil Plant Inspection Conference*, Nov. 29-Dec. 1, 1988 San Antonio, Tex.

Birring, A. S., D. G. Alcazar, J. J. Hanley, and S. Gehl, "Ultrasonic Detection of Hydrogen Damage", *Materials Evaluation* 47 Mar. 1989, pp. 345-350.

Sloat, Kim A:, and Doug Jacks, "Inspection for Hydrogen Damage in Waterwall Tubes Using Ultrasonic Techniques," Proceedings of the EPRI Conference on Failures and Inspections of Fossil-Fired Boiler Tubes, EPRI CS-3272, Bal Harbor, Florida, Apr. 1983.

B. W. Maxfield, A. Kuramoto, and J. K. Hulbert, "Evaluating EMAT Designs for Selected Applications", *Materials Evaluation*, 45 Oct. 1987 pp. 1166-1183.

*Primary Examiner*—Hezron E. Williams
*Assistant Examiner*—Rose M. Finley
*Attorney, Agent, or Firm*—Vytas R. Matas; Robert J. Edwards; Daniel S. Kalka

[57] ABSTRACT

A method and apparatus for distinguishing between hydrogen damage in the wall of a boiler tube, and surface damage on the inside surface of the tube, comprises a pair of transducers which are spaced on the outer surface of the tube and which apply a refracted shear ultrasonic wave through a chord of the tube with a beam angle that is calculated from the outside radius and wall thickness of the tube. The transducers are first applied to an undamaged tube and an instrument connected to the transducers is adjusted to 80% of full screen height. The same transducers are then, applied to a suspected boiler tube. Any attenuation of the initially high amplitude below 12 dB indicates hydrogen damage as opposed to inner surface damage which has been found to produce a far lower attenuation.

4 Claims, 2 Drawing Sheets

CONFIRMATION OF HYDROGEN DAMAGE IN BOILER TUBES BY REFRACTED SHEAR WAVES

FIELD AND BACKGROUND OF THE INVENTION

The present invention relates in general to ultrasonic testing, and in particular to a new and useful method of distinguishing between hydrogen damage in a boiler tube, and other surface conditions which give false readings that are similar to those caused by hydrogen damage.

A test for detecting hydrogen damage in fossil fired boiler tubes has been commercially utilized for several years. The test is based upon ultrasonic attenuation and has been confirmed by metallographic analysis. In some units, the test has been successfully applied to a full water wall inspection.

As a result of the large amounts of ultrasonic couplant required for a full inspection and other practical problems associated with maintaining adequate coupling, the test was modified to be performed with electromagnetic acoustic transducers (EMATs). EMATs eliminated the need for a couplant and thus allowed large areas to be scanned very rapidly. The use of EMATs also relied upon ultrasonic attenuation for the detection of damage. Both the conventional and EMAT techniques for the detection of hydrogen damage are disclosed in U.S. Pat. 4,685,344, assigned to Babcock & Wilcox, a McDermott Company.

One disadvantage of both techniques is that both techniques are sensitive to corrosion and pitting on the I.D. surface of the boiler tube. Therefore, in some instances there is no method of distinguishing between attenuation caused by actual hydrogen damage and I.D. surface conditions.

The present invention involves a supplementary technique that distinguishes between indications resulting from I.D. surface conditions and actual hydrogen damage. The inventive technique is based upon the refraction of shear waves across a chord of the boiler tube using two piezoelectric transducer wedge combinations in a pitch-catch or send-receive mode. The method of the invention also relies upon ultrasonic attenuation, however, because of the propagation path, it is relatively insensitive to the I.D. condition of the boiler tube.

The use of refracted longitudinal waves with a water column for the detection of hydrogen damage has been reported in the literature. See Sloat, Kim A., and Doug Jacks, "Inspection for Hydrogen Damage in Waterwall Tubes Using Ultrasonic Techniques," Proceedings of the EPRI Conference on Failures and Inspections of Fossil-Fired Boiler Tubes, EPRI CS-3272, Bal Harbor, Fla., April 1983. This method was tested in the original investigation leading to the present invention, and found to be impractical for field use in an actual fossil unit. The use of refracted shear and longitudinal waves as a method of introducing ultrasound into a boiler tube to measure the velocity shift resulting from multiple scattering through the microvoids of hydrogen damaged material has also been reported. See Birring, A. S., D. G. Alcazar, J. J. Hanley and S. M. Gehl, "Ultrasonic Assessment of Creep and Hydrogen Damage in Fossil Plant Components," Proceedings of the Second EPRI Fossil Plant Inspection Conference, Nov. 29-Dec. 1, 1988, San Antonio, Tex. This reference explicitly states that no ultrasonic attenuation methods are applicable for confirmation of hydrogen damage in boiler tubes. The results of feasibility tests with the present invention, however, verify the opposite. There is no known instance reported in the literature where refracted shear waves have been used for confirmation of hydrogen damage in boiler tubes.

Also, see Latimer, P. J., D. M. Stevens, and T. P. Sherlock, "A NDE Method for Hydrogen Damage Detection in Boiler Tubes," Proceedings of the EPRI Conference on Life Extension and Assessment of Fossil Plants, Wash. D.C. Jun. 2-4, 1986, EPRI CS-5208 pp. 1061-1076; Latimer, P. J. and H. L. Whaley, "Electromagnetic Transducers for Generation and Detection of Ultrasonic Waves," Accousto-Ultrasonics, Edited by John C. Duke Jr., Plenum Publishing Corporation, 1988 (Presented at the Symposium on Acousto-Ultrasonics, Jul. 12-15, 1987, Va. Polytechnic and State University, Blacksburg, Va.), and Birring, A. S., D. G. Alcazar, J. J. Hanley, and S. Gehl, "Ultrasonic Detection of Hydrogen Damage," Materials Evaluation 47 March 1989, pp. 345.

SUMMARY OF THE INVENTION

According to the present invention, sound is introduced into a boiler tube in a way that I.D. corrosion and surface roughness will have a minimal effect upon attenuating the sound. However, the presence of microvoids and innergranular cracking associated with hydrogen damage will produce significant attenuation. Piezoelectric transducers and wedges are used in a pitch-catch mode to refract the sound across a chord passing through the midwall of the boiler tube.

Hydrogen damage or attack is produced in steels exposed to a high-pressure hydrogen environment at high temperatures. Under these conditions, a chemical reaction occurs between hydrogen and carbides in the steel producing methane gas bubbles in the metal. As the bubbles grow, they interlink to form microcracks. Hydrogen damage on the I.D. of a boiler tube can cause rupturing of the tube which necessitates an immediate shutdown of the boiler.

Hydrogen damage occurring within the thickness of the tube wall, is a far more serious and dangerous condition than I.D. corrosion or surface roughness. The primary value of the present invention is thus enabling an operator to distinguish between surface irregularities and the more serious hydrogen damage. Hydrogen damage caused loss of ductility to the tube due to microfissures and decarburization. This may cause the ejection of a large segment of tube at high pressure.

Accordingly, an object of the present invention is to provide a method for distinguishing between hydrogen damage in a wall of a boiler tube, and surface damage on an inside surface of the tube, the tube having an outside radius r and a tube thickness t, the method comprising: placing a pair of ultrasonic transducers on the outside surface of an undamaged tube for sending a refracted shear wave through a chord in the wall thickness of the undamaged tube, the undamaged tube having the same outside radius and wall thickness as the boiler tube; adjusting an amplitude of the wave between the transducers to be at a relatively high amplitude; placing the transducers on the outside surface of the boiler tube at positions corresponding to the positions of the transducers on the undamaged tube; passing a refracted shear wave at the same adjusted amplitude through a chord of the boiler tube; and measuring an attenuation of the shear wave between the transducers, a relatively large attenuation being indicative of hydrogen damage and a relatively small attenuation being indicative of inside surface damage to the boiler tube.

A further object of the present invention is t provide a method wherein the chord determines the spacing between the transducers and is calculated as a function of a beam angle $\phi$, which is the angle between a tangent to the outer surface of the tube and the chord through the tube thickness between the transducers, where the chord length is equal to two times the outside tube radius, times sin $\phi$.

Another object of the present invention is to provide a method of distinguishing between hydrogen damage and surface damage on the inside diameter of the tube which is simple in design and economical to practice while using equipment which is readily available.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

BRIEF DESCRIPTION CF THE DRAWINGS

DESCRIPTION OF THE PREFERRED EMBODIMENT

Figure 2:
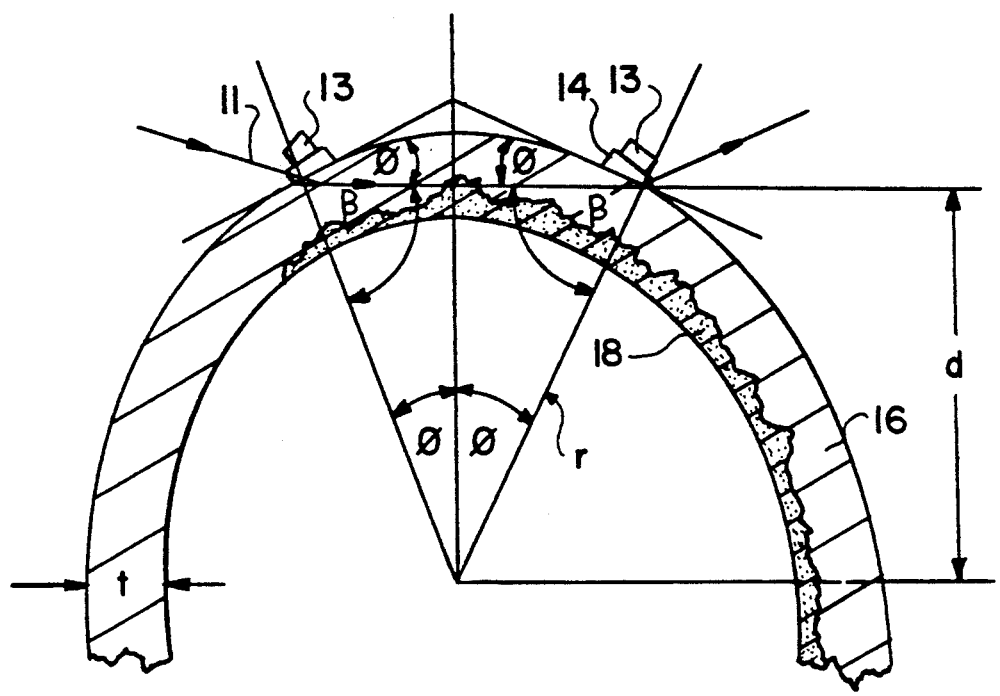
FIG. 2 is a sectional view through a damaged boiler tube showing the geometry used for practicing the present invention.
Figure 3:
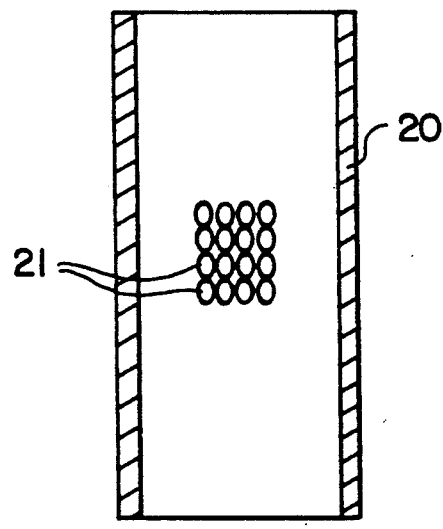
FIG. 3 is a schematic sectional view showing artificial surface damage on a tube which was used to confirm the operability of the present invention.

Referring to the drawings in particular, the invention embodied therein comprises a method for distinguishing between hydrogen damage shown at 18 in FIG. 2, which invades the wall thickness of a boiler tube 16, and surface irregularities exemplified by flat bottomed milled bores 21 shown in an otherwise undamaged tube 20 in FIG. 3, which was utilized to confirm the operability of the present invention.

The geometry of the inventive technique is illustrated in FIG. 2. Referring to FIG. 2:
Let;
r = outer radius of tube
t = thickness of the wall
then;

$$\cos \phi = (r - t/2)/r \quad (1)$$

$$\beta = 90° - \phi \quad (2)$$

$$\beta = \text{refraction angle} \quad (3)$$

$$\text{Chord} = 2r \sin \phi \quad (4)$$

Therefore, the angle of refraction is determined by the radius r of the tube and the wall thickness &as shown by equation (1) and (2). The separation of the entrance and exit points is given by the length of the chord in equation (4).

Figure 1:
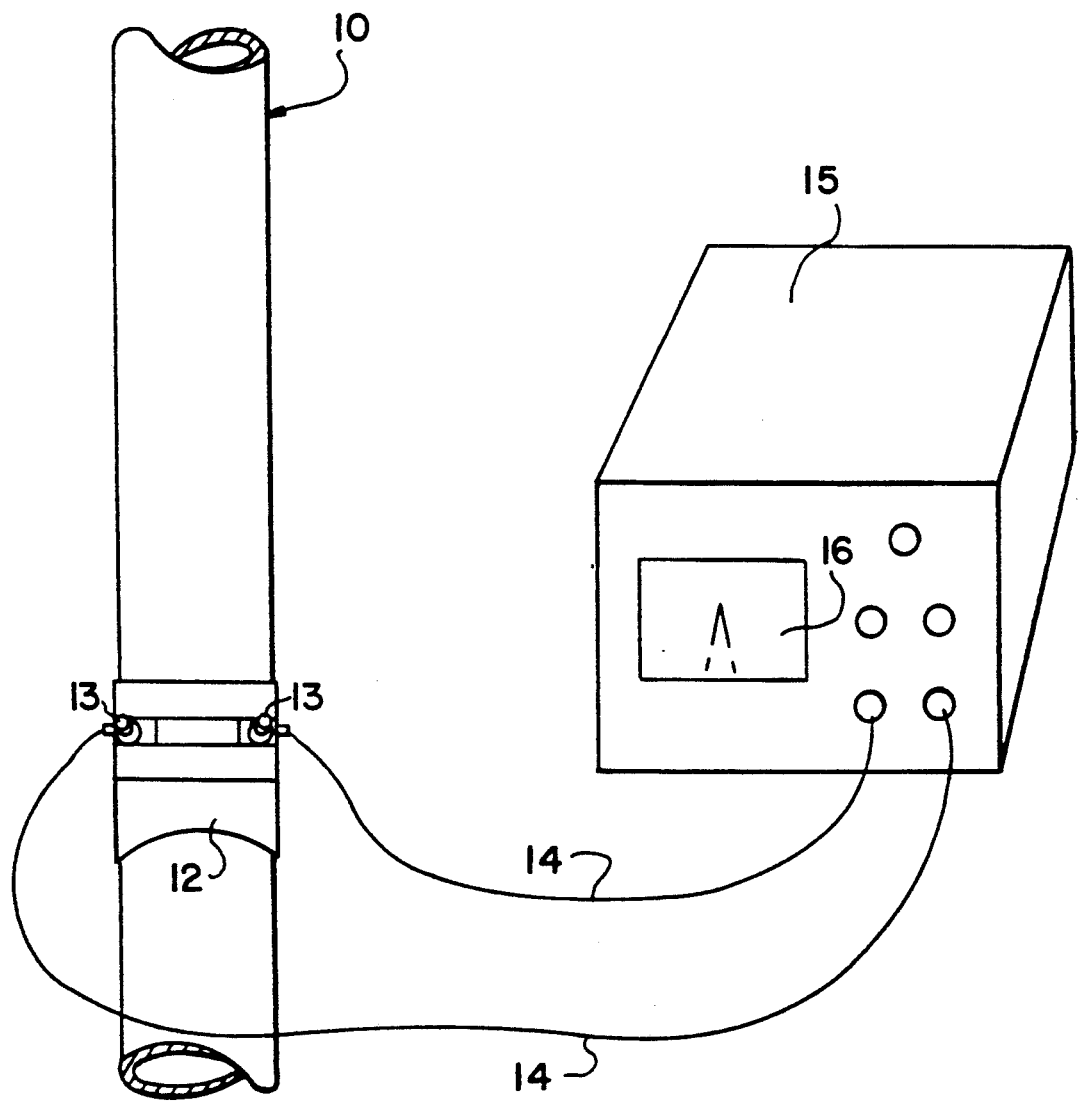
FIG. 1 is a schematic representation of the apparatus used to practice the present invention.

The apparatus is shown in FIG. 1. In practice, two 5 MHz, 0.25"×0.25" miniature transducers 13, 13 are used. The same field instrument 15, ultrasonic couplant, and fixtures 12 are used as with the conventional technique. The fixture 12 is placed on an undamaged tube 10. The signal on a scope display 16 is set to 80% full screen height (FSH). This process is repeated on several tubes to insure that the amplitude remains at 80% FSH. The fixture is then placed on the tube in question 16 in FIG. 2. An attenuation of 12 dB or greater is an indication of significant hydrogen damage 18 in tube 16.

The use of refracted shear waves provides the following advantages over other techniques for confirmation of hydrogen damage:

(a) The velocity shift technique is difficult to interpret. It is slow and relies upon very accurate measurements of velocity under crude field conditions. In contrast, the refracted shear wave technique of the invention is very easy to interpret since it only involves observing the decrease in ultrasonic signal amplitude in damaged material.

(b) The average time required to confirm an indication is approximately two minutes.

(c) The inventive technique can be performed with the same field scope and fixture that is now being used in the conventional technique.

(d) A technical person can be easily trained to perform the test.

(e) The inventive technique uses the combination of wedges and couplant that Babcock & Wilcox used successfully in the field for the last few years.

(f) In many fossil units, I.D. pitting is prevalent but not serious enough to justify tube removal. In those cases, this technique would be invaluable in identifying tubes with the serious failure mechanisms.

In greater detail, transducers 13, 13 in FIG. 2 are applied to the outside surface of a tube, whether it is the undamaged tube 10 to establish the amplitude adjustment for the ultrasonic refracted shear waves, or the suspected boiler tube 16 in FIG. 2, at a spacing corresponding to the chord along which the sound path 11 shown in FIG. 2 passes through the middle of the wall thickness of the tube 16. Each transducer is mounted on a wedge shaped shoe 14 which has an inner surface machine to the contour of the outer diameter of the tube.

For tubes having an outside diameter of 3.04 inches and a wall thickness of 0.250 inches, and utilizing equation (1) through (4), the chord angle $\phi = 23.4°$.

In FIG. 1, field instrument 15 may be a commercially available USL-38 instrument or a Krautkramer US1P-12 instrument.

The fixture 12 is advantageously a Lucite (a trademark) material block structure which mounts the transducers and shoes. The fixture is provided with a curved lower surface which precisely matches the outer surface of the tube for bringing the transducer shoes into close contact with the outer surface of the tube as shown in FIG. 2.

The technique of the invention was tested on various samples with artificial corrosion such as illustrated in FIG. 3. The technique was also tried on a variety of boiler tubes with various degrees of I.D. corrosion and hydrogen damage. Metallographic examination confirmed the reliability of this technique in distinguishing between hydrogen damage and fluid side corrosion. In FIG. 3, the I.D. of tube 20 is shown milled with holes 21 which were 50 mils deep in one test and 25 mils in another.

While a specific embodiment of the invention has been shown and described in detail to illustrate the application of the principles of the invention, it will be understood that the invention may be embodied otherwise without departing from such principles.

What is claimed is:

1. A method for distinguishing between hydrogen damage in a wall of a boiler tube, and other surface conditions which can give false indications of hydrogen damage on an inside surface of the tube, the tube having an outside radius r and a wall thickness t, the method comprising the steps of:

placing a pair of ultrasonic transducers on an outside surface of an undamaged tube for sending a refracted shear wave through a chord in the wall thickness of the undamaged tube, the undamaged tube having the same outside radius and wall thickness as the boiler tube, the chord determining a spacing between the transducers and being calculated as a function of a beam angle $\phi$, which is the angle between a tangent to the outer surface of the tube and the chord through the wall thickness between the transducers, where the chord length is equal to two times the outside tube radius r, times sin $\phi$;

adjusting an amplitude of the wave between the transducers to be about 80% full screen height;

placing the transducers on an outside surface of the boiler tube at positions corresponding to the positions of the transducers of the undamaged tube;

passing a refracted shear wave at the same adjusted amplitude through a chord of the boiler tue corresponding to the chord of the undamaged tube; and measuring an attenuation of the shear wave between the transducers, a relatively large attenuation being indicative of hydrogen damage and a relatively small attenuation being indicative of other surface conditions inside the boiler tube.

2. A method according to claim 1, including utilizing an instrument having a screen display to display signal amplitude, to generate and measure the ultrasonic waves, the adjusted amplitude corresponding to approximately 80% of a full screen height for the display.

3. A method according to claim 2, wherein the attenuation which is indicative of hydrogen damages is at least 12 db.

4. An apparatus for distinguishing between hydrogen damage in a wall of boiler tube and other surface conditions which can give false indications of hydrogen damage on an inside surface of the boiler tube, the boiler tube having an outside radius r and a wall thickness t, the apparatus comprising:

a pair of ultrasonic transducers spaced from each other by a chord which is calculated as a function of a beam angle $\phi$ between a tangent to an outside surface of the tube and the chord, wherein the chord length equals two items the outside radius r, times sin $\phi$, one of said transducers sending a refracted shear wave through the chord of the boiler tube to be received by the other transducers;

a fixture to which the transducers are fixed, the fixture having a tube contact surface and which matches a contour of the outside surface of the tube; and means for measuring attenuation of an amplitude for the refracted shear wave for distinguishing between hydrogen damage in the boiler tube and other surface conditions on the inside surface of the boiler tube which can give false indications of hydrogen damage.

* * * * *